(12) United States Patent
Hone et al.

(10) Patent No.: US 12,728,060 B2
(45) Date of Patent: Sep. 8, 2026

(54) POSITIONERS AND RELATED METHODS

(71) Applicant: After-Life Care LLC, Santaquin, UT (US)

(72) Inventors: Melissa Hone, Santaquin, UT (US); Riley Glen Hone, Santaquin, UT (US)

(73) Assignee: After-Life Care LLC, Santaquin, UT (US)

( * ) Notice: Subject to any disclaimer, the term of this patent is extended or adjusted under 35 U.S.C. 154(b) by 0 days.

(21) Appl. No.: 18/400,479

(22) Filed: Dec. 29, 2023

(65) Prior Publication Data

US 2024/0216207 A1 Jul. 4, 2024

Related U.S. Application Data

(60) Provisional application No. 63/477,809, filed on Dec. 29, 2022.

(51) Int. Cl.
*A61G 17/04* (2006.01)
*A61F 5/56* (2006.01)

(52) U.S. Cl.
CPC ............ *A61G 17/044* (2016.11); *A61F 5/566* (2013.01)

(58) Field of Classification Search
CPC ................ A61G 17/044; A61G 13/121; A61G 13/1215; A61F 5/566; A61F 5/055; A61F 5/56
USPC ..................................................... 27/13, 25.1
See application file for complete search history.

(56) References Cited

U.S. PATENT DOCUMENTS 378,207 A * 2/1888 McGrath .............. A61G 17/044 27/13
D33,352 S 10/1900 Warren
1,000,907 A * 8/1911 Hammond ........... A61G 17/044 433/68

(Continued)

FOREIGN PATENT DOCUMENTS

DE 20121093 U1 * 5/2002 ............... A61F 5/56
KR 3011447640000 12/2021

(Continued)

OTHER PUBLICATIONS

Neck Stretcher, Online, Published date Mar. 7, 2024, Retrieved (by patent examiner in another case) on Sep. 10, 2024 from URL: https://www.amazon.com/Stretcher-Whiplash-Adjustable-Sleeping-Universal/dp/B0D95LRLRF (Year: 2024).

(Continued)

*Primary Examiner* — William L Miller
(74) *Attorney, Agent, or Firm* — Law Office of Paul B. Johnson; Paul B. Johnson

(57) ABSTRACT

A positioner may include a compressible member forming a main body, two arms extending from the main body, and a top. The main body may have an average circumference greater than an average circumference of each arm. The compressible member may include a covering at least partially filled with a filler. A plurality of straps may be secured to the compressible member. The positioner may be secured around a neck of a deceased person such that the main body secures a mouth of the deceased person closed and the main body and arms position a head of the deceased person in a substantially fixed position, such as for a funeral viewing. The positioners may also be used on a living person to reduce or eliminate snoring.

1 Claim, 9 Drawing Sheets

(56) References Cited

U.S. PATENT DOCUMENTS 1,216,679 A * 2/1917 Foster .................... A61F 5/566 128/848
1,845,853 A * 2/1932 Sweeney ................. A01N 1/00 27/13
2,911,970 A * 11/1959 Bartels ................... A61F 5/055 602/18
3,135,256 A 6/1964 Gruber
3,497,872 A 3/1970 Mitchell
3,657,739 A * 4/1972 Holmes, Sr. ....... A41D 13/0512 2/467
3,850,164 A * 11/1974 Hare ...................... A61F 5/055 602/18
4,232,663 A * 11/1980 Newton .................. A61F 5/055 602/18
4,475,543 A * 10/1984 Brooks ................... A61F 5/028 602/19
4,958,631 A 9/1990 Sarkozi
5,265,624 A * 11/1993 Bowman .............. A61N 1/3601 600/537
5,275,581 A * 1/1994 Bender ................... A61F 5/055 602/5
D353,205 S * 12/1994 Canavan ..................... D24/206
D369,660 S 5/1996 Myoga
5,515,867 A * 5/1996 Lamb ..................... A61G 13/12 128/845
D379,232 S 5/1997 Brooke
5,904,662 A * 5/1999 Myoga .................... A61F 5/055 602/18
6,056,711 A * 5/2000 Domanski ............... A61F 5/055 602/18
6,071,256 A 6/2000 Lam
D469,541 S 1/2003 Cheatham
D519,639 S 4/2006 Follman
D556,333 S 11/2007 Hoffman et al.
D582,045 S 12/2008 James
7,789,843 B2 * 9/2010 Ray ......................... A61F 5/055 602/17
D627,893 S 11/2010 Weiss
D630,335 S 1/2011 Wise et al.
8,382,692 B1 * 2/2013 Chao ...................... A47C 7/383 602/17
D677,797 S 3/2013 Godfrey et al.
8,469,032 B2 * 6/2013 Farnum .............. A61G 13/1215 602/17
10,154,697 B2 * 12/2018 Kasahara ............ A61F 5/05816
D841,825 S 2/2019 Rogers
10,413,303 B2 * 9/2019 Smith ................ A63B 71/1291
10,842,502 B2 * 11/2020 Smith ................ A61B 17/1325
D910,340 S * 2/2021 Cato ............................. D6/601
D926,988 S * 8/2021 Henderson ................... D24/162
11,413,183 B2 8/2022 Nibhanipudi
D978,486 S 2/2023 Wise
11,696,766 B2 * 7/2023 Smith .................... A61B 90/08 606/202
D1,007,142 S * 12/2023 Malick .......................... D3/226
D1,030,074 S 6/2024 Cao
D1,040,521 S 9/2024 Yoshida
D1,079,017 S * 6/2025 Hone ........................... D24/184
2005/0102758 A1 5/2005 Ramsbottom et al.
2007/0006886 A1 * 1/2007 Bates .................. A61G 17/044 128/857
2007/0256694 A1 * 11/2007 Kussick .................... A61F 5/56 128/848
2008/0223377 A1 * 9/2008 Kussick .................... A61F 5/56 128/869
2010/0294284 A1 * 11/2010 Hohenhorst ............ A61F 5/012 128/848
2010/0307512 A1 * 12/2010 Krook ....................... A61F 5/56 128/848
2013/0035624 A1 * 2/2013 Mroz ...................... A61F 5/055 602/18
2013/0333708 A1 * 12/2013 Hassan ..................... A61F 5/56 128/848
2014/0076331 A1 * 3/2014 Cho ..................... A61G 13/121 128/845
2014/0142616 A1 * 5/2014 Smith .................... A61B 90/08 606/202
2014/0276278 A1 * 9/2014 Smith ................ A63B 71/1291 601/133
2014/0298566 A1 * 10/2014 Rogers .................. A61M 35/10 2/171.2
2017/0239076 A1 * 8/2017 Stanton ................. A61F 5/3707
2020/0051705 A1 2/2020 Bernstein et al.
2020/0390629 A1 * 12/2020 Sifferlin ............... A61G 13/129

FOREIGN PATENT DOCUMENTS

WO WO-2015109370 A1 * 7/2015 ............... A61F 5/37
WO WO-2023208789 A1 * 11/2023 ............. A61F 5/055

OTHER PUBLICATIONS

JenPen Pillow, Online, Published date Sep. 8, 2024, Retrieved on Aug. 7, 2025 by examiner in another patent case from URL: https://www.amazon.com/Headrest-Airplane-Functional-Sleeping-Microbead/dp/B09FPPHWT4/ (Year: 2024).

* cited by examiner 232
200
202
240
206
230

234
236
216
220
218
210
214
224
222
208

POSITIONERS AND RELATED METHODS

CROSS REFERENCE TO RELATED APPLICATIONS

This document claims the benefit of the filing date of U.S. Provisional Patent Application No. 63/477,809, entitled "Positioners and Related Methods," naming as first inventor Melissa Hone, which was filed on Dec. 29, 2022, the disclosure of which is hereby incorporated entirely herein by reference.

BACKGROUND

1. Technical Field

Aspects of this document relate generally to devices and methods for positioning the head of a deceased person in a fixed or relatively fixed position. Other aspects relate generally to positioning a living person's head for reducing or eliminating snoring.

2. Background Art

The bodies of deceased persons are sometimes made available for viewing prior to burial. Such viewings often involve placing the deceased person in a lying position in an open casket. In some cases it may be difficult to properly position the head, neck and/or jaw of the deceased person to positions that are desirable for the viewing. Rolled-up towels have at times been used to assist in positioning a deceased person's head, neck and/or jaw to positions desirable for a viewing—for example in an attempt to keep the deceased person's mouth closed during the viewing.

Additionally, various devices exist for attempting to reduce snoring during sleeping, each of which has its own tradeoffs and limitations, and many of which do not effectively reduce or eliminate snoring during sleeping.

SUMMARY

In implementations, the devices described herein relate to a positioner, including: a compressible member forming a main body and two arms each extending from the main body, the compressible member also forming a top; wherein the main body has an average circumference circumscribing the top and a bottom of the main body, and perpendicular with the top of the main body; wherein each arm has an average circumference circumscribing the top and a bottom of the arm, and perpendicular with the top; wherein the average circumference of the main body is greater than the average circumference of each arm; and wherein the compressible member includes a covering at least partially filled with a filler; and a plurality of straps secured to the compressible member and extending therefrom; wherein the positioner is configured to be secured around a neck of a person such that the main body secures a mouth of the person closed and the main body and arms position a head of the person in a substantially fixed position.

In implementations, the devices described herein relate to a positioner, further including a pair of couplers, each coupler coupled with one of the straps, wherein the couplers are configured to be releasably secured together.

In implementations, the devices described herein relate to a positioner, wherein at least one of the straps is manually adjustable to multiple lengths using one of the couplers.

In implementations, the devices described herein relate to a positioner, wherein the filler includes one or more of: a compressible foam, cotton, wool, feathers, down, shredded paper, shredded cardboard, and polymer beads.

In implementations, the devices described herein relate to a positioner, wherein the main body and the arms form a T-shape.

In implementations, the devices described herein relate to a positioner, wherein the filler consists of a single solid piece of compressible material.

In implementations, the devices described herein relate to a positioner, wherein the filler substantially fills the main body and also substantially fills each arm.

In implementations, the devices described herein relate to a positioner, wherein the filler substantially fills the main body but fills less than half of each arm.

In implementations, the devices described herein relate to a positioner, wherein the bottom of each arm includes a curved section.

In implementations, the techniques described herein relate to a method of positioning a person, including: positioning a main body of a positioner between a chin and upper chest of the person; wherein the positioner includes: a compressible member forming the main body and two arms each extending from the main body; and a plurality of straps secured to the compressible member and extending therefrom; positioning each arm at least partially around a neck of the person; and securing each arm in a fixed configuration using the straps, thereby securing the positioner in a position to secure a mouth of the person closed and to secure a head of the person in a substantially fixed position.

In implementations, the techniques described herein relate to a method, wherein: the compressible member includes a top; the main body has an average height from the top to a bottom of the main body, and perpendicular with the top; each arm has an average height from the top to a bottom of the arm, and perpendicular with the top; and the average height of the main body is greater than the average height of each arm.

In implementations, the techniques described herein relate to a method wherein the compressible member includes a fabric at least partially filled with a filler.

In implementations, the techniques described herein relate to a method, wherein the filler includes a compressible foam.

In implementations, the techniques described herein relate to a method, wherein the positioner further includes a pair of buckles, each of the buckles coupled with one of the straps, wherein at least one of the straps is manually adjustable to multiple lengths using a slip lock of one of the buckles, and wherein the buckles are configured to be releasably secured together.

In implementations, the techniques described herein relate to a method, further including securing the buckles together at a back of the neck of the person.

In implementations, the techniques described herein relate to a method, wherein the person is deceased and the method includes positioning the person for a funeral viewing.

In implementations, the techniques described herein relate to a method, wherein the person is living and the method includes reducing or eliminating snoring of the person during sleep.

In implementations, the devices described herein relate to a positioner, consisting of: a compressible member forming a main body and two arms each extending from the main body, the compressible member including a covering at least partially filled with a filler; a plurality of straps secured to the compressible member and extending therefrom, and; a plurality of couplers, each coupled to one of the straps, the couplers configured to be releasably secured together to secure the positioner around a neck of a person such that the main body secures a mouth of the person closed and the main body and arms position a head of the person in a substantially fixed position.

In implementations, the devices described herein relate to a positioner, wherein at least one of the couplers includes an adjustment mechanism configured to allow manual adjustment of one of the straps to multiple lengths.

In implementations, the devices described herein relate to a positioner, wherein the covering includes a fabric and one or more seams formed with stitching, and wherein the filler includes one or more of: a compressible foam, cotton, wool, feathers, down, shredded paper, shredded cardboard, and polymer beads.

General details of the above-described implementations, and other implementations, are given below in the DESCRIPTION, the DRAWINGS, the CLAIMS and the ABSTRACT.

BRIEF DESCRIPTION OF THE DRAWINGS

Implementations will be discussed hereafter using reference to the included drawings, briefly described below, wherein like designations refer to like elements. The drawings are not necessarily drawn to scale.

DESCRIPTION

Implementations/embodiments disclosed herein (including those not expressly discussed in detail) are not limited to the particular components or procedures described herein. Additional or alternative components, assembly procedures, and/or methods of use consistent with the intended positioners and related methods may be utilized in any implementation. This may include any materials, components, subcomponents, methods, sub-methods, steps, and so forth.

Implementations of positioners and related methods relate to devices and methods for supporting or holding the head, neck, jaw, and/or mouth of a deceased person in a desired configuration for funeral viewings and/or in other settings.

Figure 1:
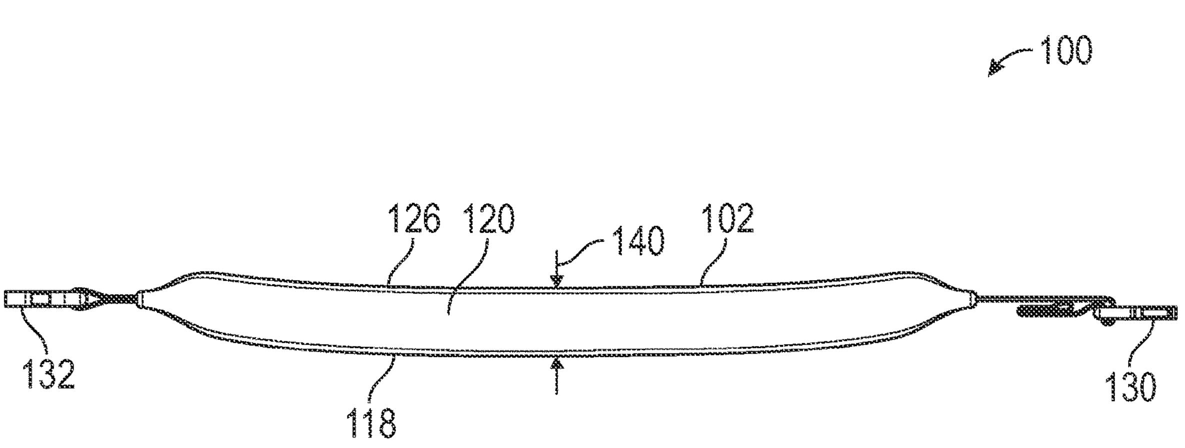
FIG. 1 is a top view of an implementation of a positioner in an open configuration.
Figure 2:
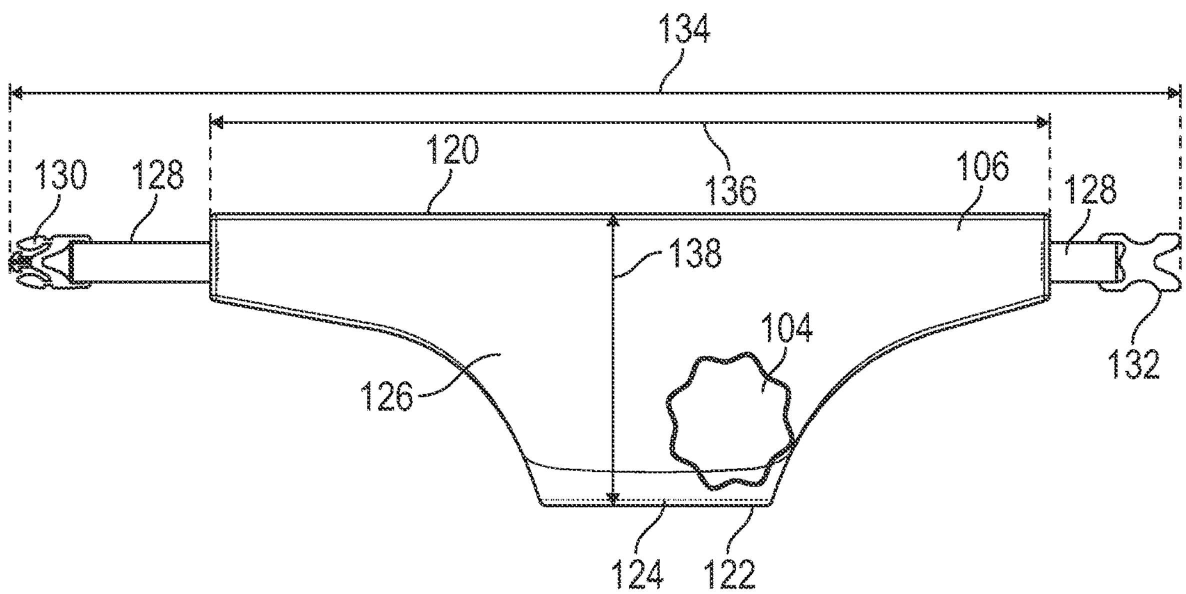
FIG. 2 is a rear partial-cutaway view of the positioner of FIG. 1 in the open configuration.
Figure 3:
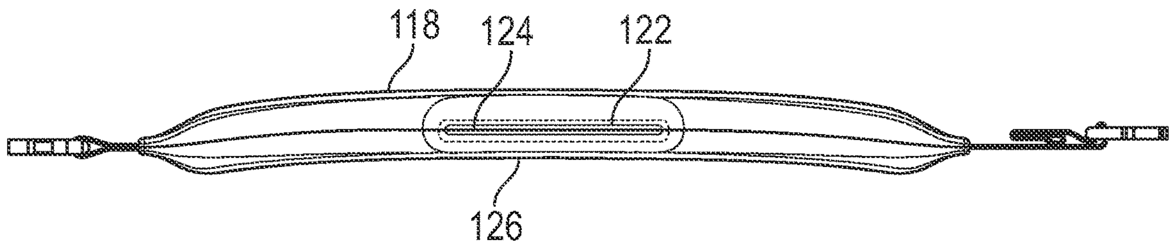
FIG. 3 is a bottom view of the positioner of FIG. 1 in the open configuration.
Figure 4:
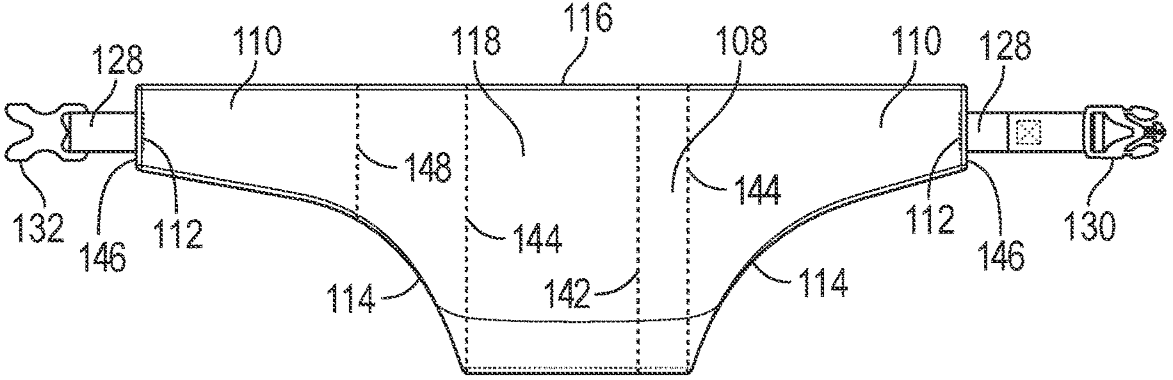
FIG. 4 is a rear view of the positioner of FIG. 1 in the open configuration.
Figure 5:
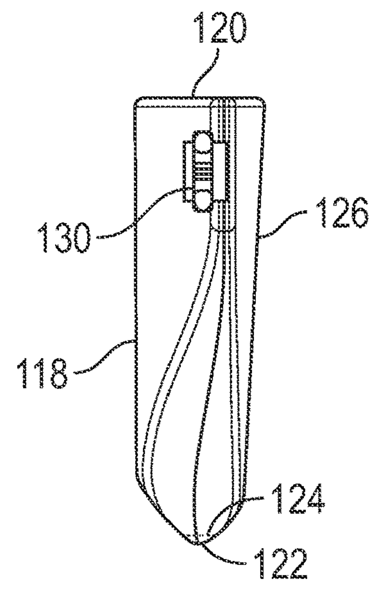
FIG. 5 is a right-side view of the positioner of FIG. 1 in the open configuration.
Figure 6:
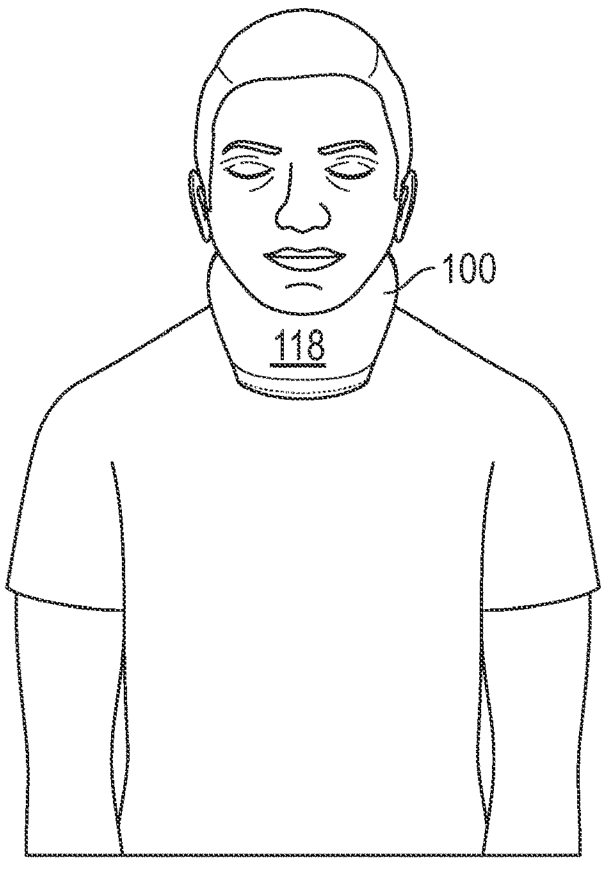
FIG. 6 is a front, top view of the positioner of FIG. 1 in a closed configuration secured around a neck of a person.
Figure 7:
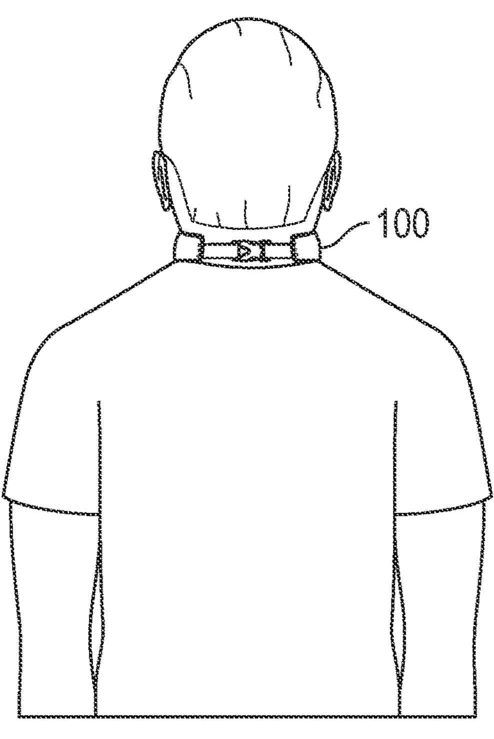
FIG. 7 is a rear view of the positioner of FIG. 1 in the closed configuration secured around the neck of the person of FIG. 6.
Figure 8:
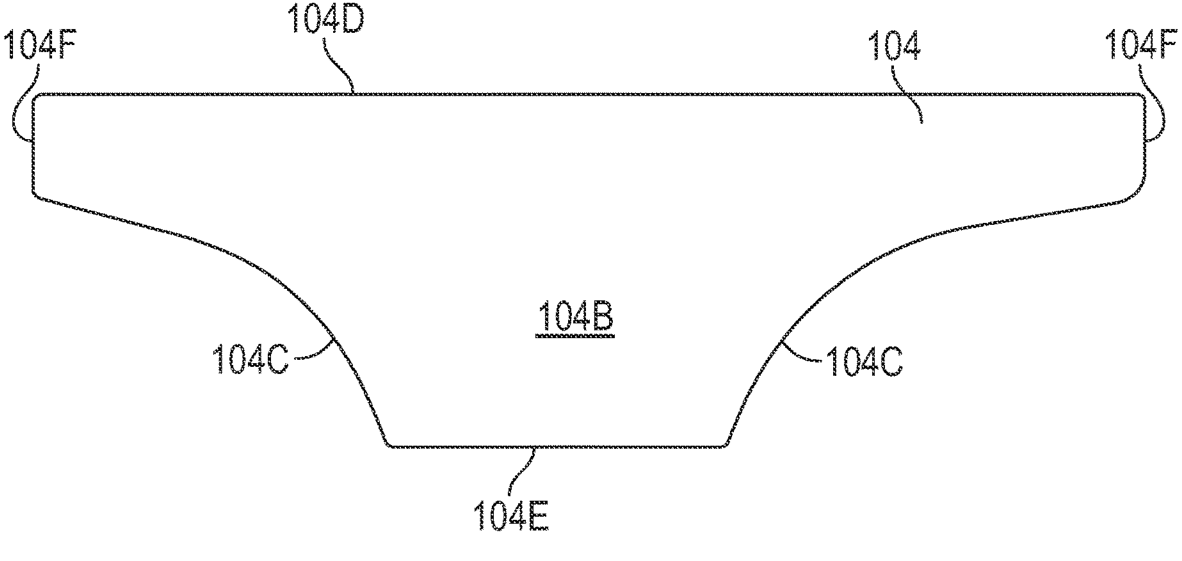
FIG. 8 is a rear view of an implementation of a filler of the positioner of FIG. 1.
Figure 9:
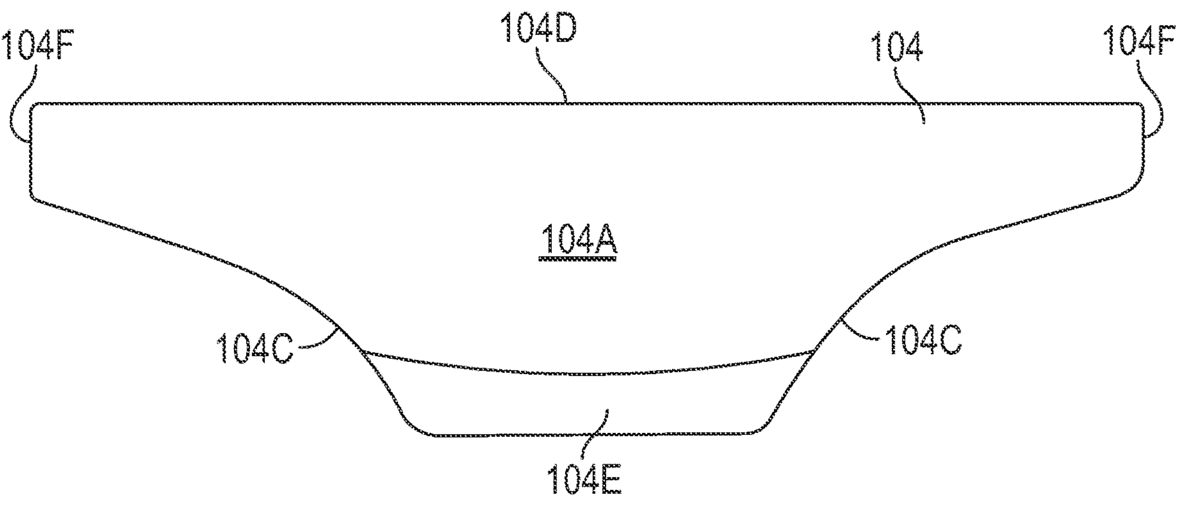
FIG. 9 is a front view of the filler of FIG. 8.
Figure 10:
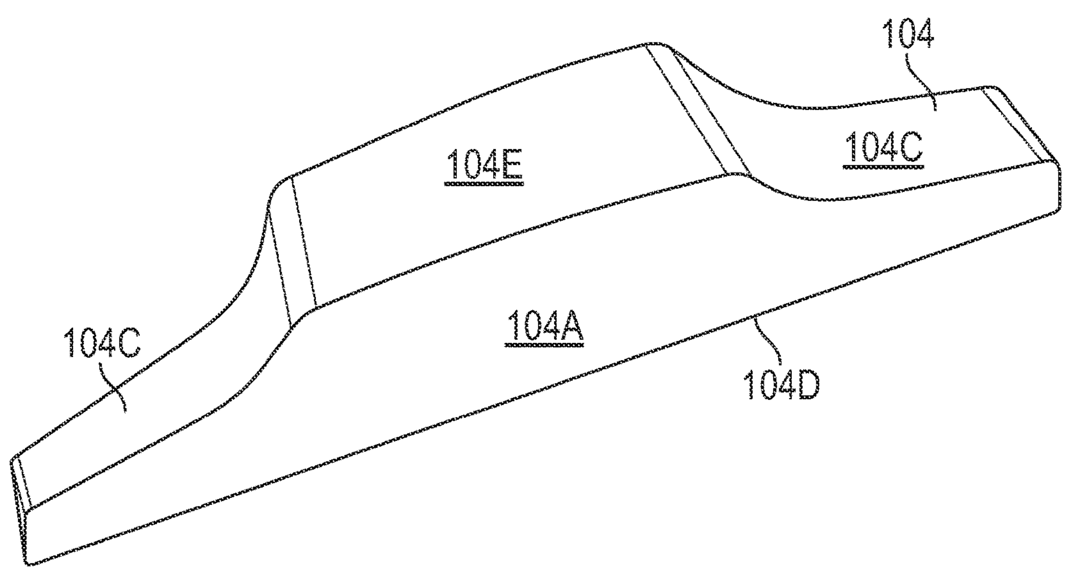
FIG. 10 is a front, bottom, right-side view of the filler of FIG. 8.

Referring now to FIGS. 1-10, a first implementation of a positioner, and implementing components, are shown. FIG. 1 shows a top view of positioner 100 in an open configuration. FIG. 2 shows a rear partial cutaway view of the positioner in the open configuration. FIG. 3 shows a bottom view of the positioner in the open configuration. FIG. 4 shows a rear view of the positioner in the open configuration. FIG. 5 shows a right-side view of the positioner in the open configuration. FIG. 6 shows a front, top view of the positioner in a closed configuration secured around a neck of a person. FIG. 7 shows a rear view of the positioner in the closed configuration secured around the neck of the person. FIG. 8 shows a rear view of a filler 104 of the positioner, which in this example is a foam insert. FIG. 9 shows a front view of the filler. FIG. 10 shows a front, bottom, right-side view of the filler.

FIG. 1 shows a top 120 of a compressible member 102 of the positioner 100. There is some curvature to the compressible member so that a front 118 of the compressible member bows outward or is convex while the back 126 of the compressible member bows inward or is concave. This is optional, and in some cases there may be no such curvature. Even so, the compressible member may be flexible and soft, similar to a pillow (and indeed in implementations the compressible member may be or may include a uniquely shaped pillow), such that it may be easily bent and deformed manually during a positioning operation. The compressible member includes the filler 104 (see FIG. 2) covered with a covering 106. The covering may be formed of any type of fabric, such as cotton, wool, a polymer-based fabric, and so forth. The filler may be made of a polymeric foam but in other implementations could be a non-foam material, such as cotton, wool, feathers or down, shredded or other small paper or soft cardboard elements, polymer beads, and so forth. The purpose of the filler is to provide some cushioning and loft, but also to allow some deformation of the compressible member. For example, the filler allows the compressible member to deform some when the positioner is placed around a person's neck and/or when a person's chin or jaw rests against it.

An example filler, which in this case is a foam insert, is shown in FIGS. 8-10. This is only one example, and other configurations are possible. The example filler includes a front 104A, back 104B, curved side portions 104C, top 104D, bottom 104E, and sides 104F. There may be somewhat smooth, curved transitions between some of these portions and/or abrupt transitions between some of the portions. The bottom 104E is at an angle so that it is visible from the front view in FIG. 9, but in other implementations it could face directly downward instead. The filler of FIGS. 8-10 is generally shaped and sized to fully fill the covering of the compressible member, including a main body 108 and both arms 110 of the compressible member.

The positioner may include one or more seams, such as seams 112 proximate terminal ends of the arms of the compressible member and bottom seam 124 proximate a bottom 122 of the compressible member. The seams may be used to close openings in the covering after a filler is placed within the covering. The seams may, additionally or alternatively, be used to sew other elements to the compressible member. For example, seams 112 may be used to attach straps 128 to the arms of the compressible member. The straps are attached or coupled to couplers 130 and 132, which couplers in the examples in the drawings jointly form a side release buckle. One or more of the couplers may be adjustably coupled with its corresponding strap such that a length of the strap between the coupler and the compressible member may be adjusted as desired. This may be accomplished, for example, by including slip lock elements or tri-glide elements in the couplers (or elsewhere coupled with the straps). In the figures only the strap passing through coupler 130 is adjustable, coupler 130 including a slip lock such that the strap can be adjusted by positioning the coupler 130 in a certain position relative to the strap, but in other positions of the coupler relative to the strap (such as the in-use position when attached around a user's neck) the strap and coupler remain secured relative to one another so that the coupler does not slide to a different position along the strap. Couplers 130 and 132 in the examples in the drawings are male and female side release buckle elements, respectively. Other configurations are possible—for example the straps could have no couplers but could simply be tied together behind a person's neck, or they could have hook-and-loop fasteners thereon for tightening, or they could be rope-like elements (instead of straps) configured to be tied behind a person's neck, and so forth.

The compressible member is seen to have a straight (or substantially straight) section 116 and two curved sections 114. As used herein, the term "substantially straight" refers to a section wherein all portions between ends of the section are within a ten-degree range of either end. Due to the straight (or substantially straight) section and the curved sections, the compressible member forms an overall T-shape. This shape is useful for use on a deceased person in that the main body of the compressible member may rest between the person's chin/jaw and chest (and/or also abutting the neck therebetween) and the arms may be strapped around the sides of the person's neck (the straps buckled behind the user's neck). This configuration is shown in FIGS. 6-7.

Such a configuration solves an issue with presentation of deceased persons for viewing. A deceased person's jaw and mouth tend to open of their own accord, and this is generally not desirable for viewing (such as at funeral viewings). The positioners disclosed herein are useful for positioning the deceased person's head, neck, jaw and/or chin so that, when the deceased person is lying flat in a coffin/casket the deceased person's head is kept straight and the person's jaw and mouth remain closed, as is generally desired. In other viewing positions, such as when the deceased person's upper body and/or head are somewhat elevated (such as through a pillow or the like), the positioners can again keep the head, neck, jaw and/or chin properly positioned, so that for example the jaw and mouth remain closed. The T-shape of the positioner, due to the shape of the main body portion relative to the arms, provides sufficient volume between the user's chin or jaw and chest such that the main body abuts both the chin and the chest to keep the head positioned and the jaw/mouth closed, as desired.

Rolled-up towels have at times been used for a purpose similar to that disclosed herein, in an attempt to keep a deceased person's mouth closed, but rolled-up towels do not provide the unique functions and advantages of the positioners disclosed herein. Once the positioner is wrapped around the user's neck, as in FIG. 6, the couplers can be buckled together (as seen in FIG. 7) so that the positioner is secured in a closed position. One or both of the straps may then be tightened so that the positioner is in a secure configuration relative to the person's neck. Alternatively, the one or more straps may be tightened prior to buckling the couplers together. Although specific buckle types are shown in the drawings, any type of bucklers or couplers may be used for couplers 130/132.

The positioner may be external to the deceased person's clothing, as in FIGS. 6-7, though in some implementations it could also be secured underneath clothing. The covering 106 could have any color or design to blend well with the deceased person's clothing or appearance or to otherwise not distract from a funeral viewing, for example. FIGS. 2, 4 and 5 show that there is some curvature at the bottom 122 of the compressible member (from front to back of the compressible member), though in some cases this curvature may not be present and the bottom 122 could be relatively flat. Various configurations and modifications could be made without departing from the spirit and scope of this disclosure. However, as described above, the T-shape of the compressible member is useful for the reasons given herein.

Although the positioners are described herein as being particularly useful for use with deceased persons, and/or for pre-burial viewings, there may be other uses for the positioners both with respect to deceased and with respect to non-deceased persons.

Positioner 100 has a number of dimensions which may be modified as desired. For example, different deceased persons having different body sizes, neck sizes, and so forth may benefit from different-sized positioners. Each positioner includes an overall length 134 (which may be adjusted from a maximum overall length, with the straps fully extended, to a minimum overall length with the straps fully shortened), a length 136 of the compressible member only, a height 138, and a thickness 140.

Figures 11, 12:
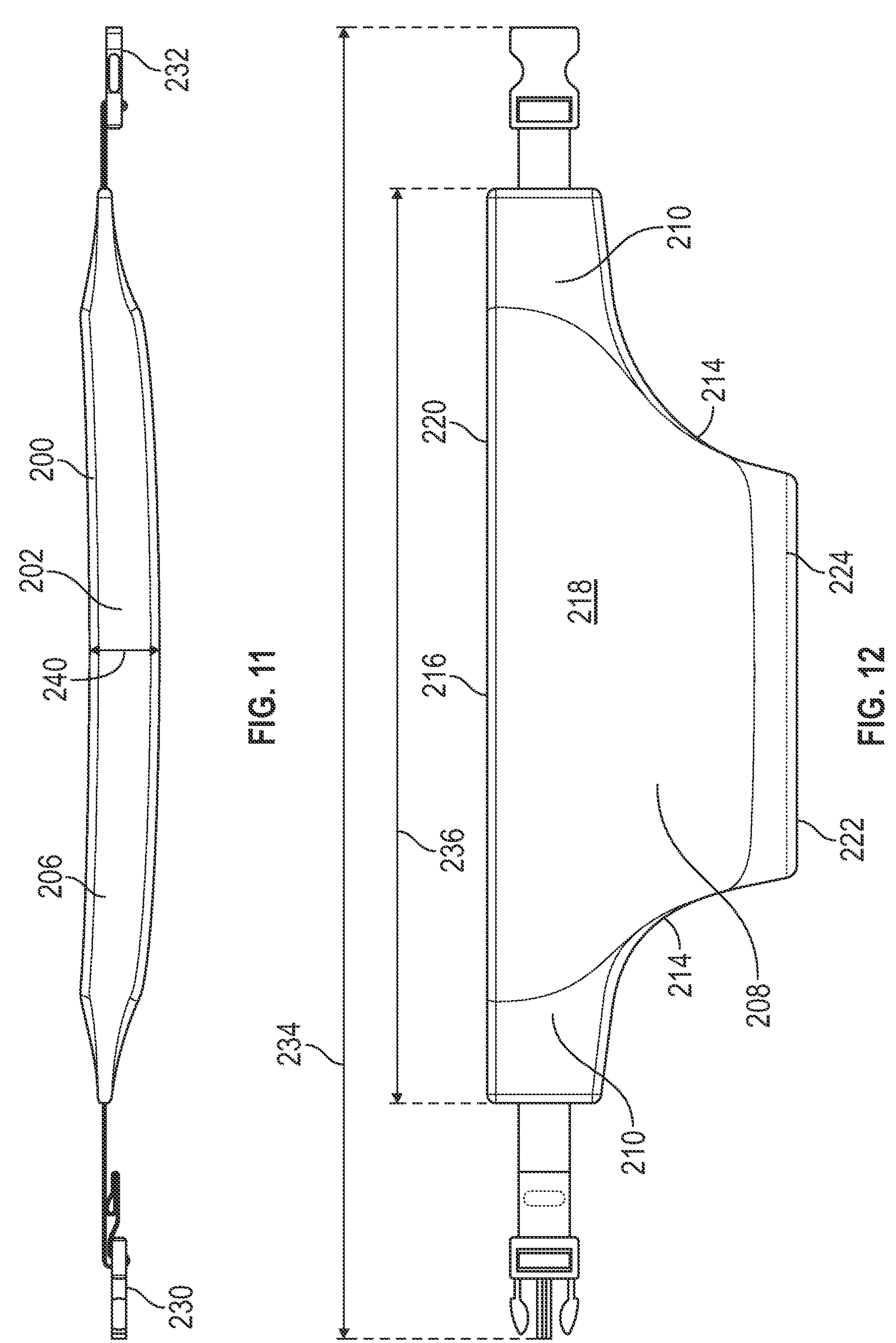
FIG. 11 is a top view of another implementation of a positioner in an open configuration.
FIG. 12 is a front view of the positioner of FIG. 11 in the open configuration.
Figure 13:
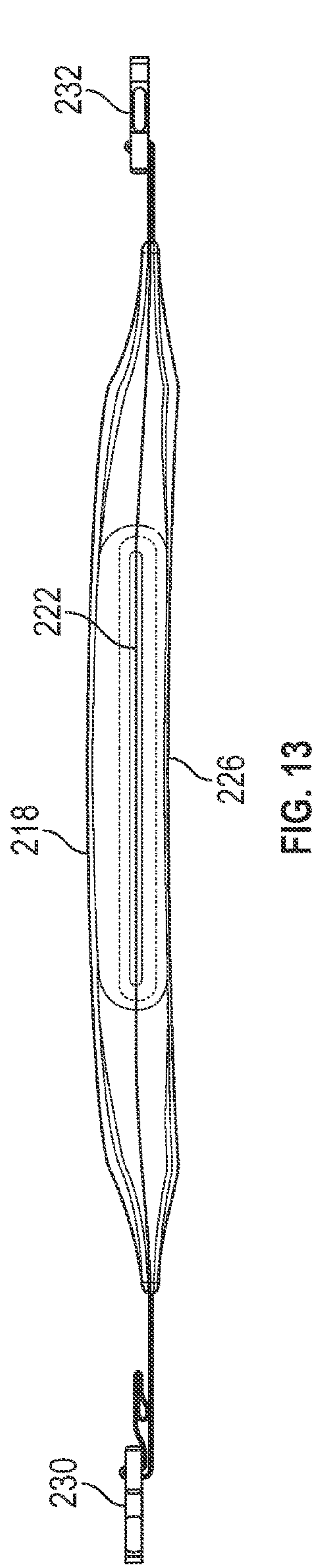
FIG. 13 is a bottom view of the positioner of FIG. 11 in the open configuration.
Figure 14:
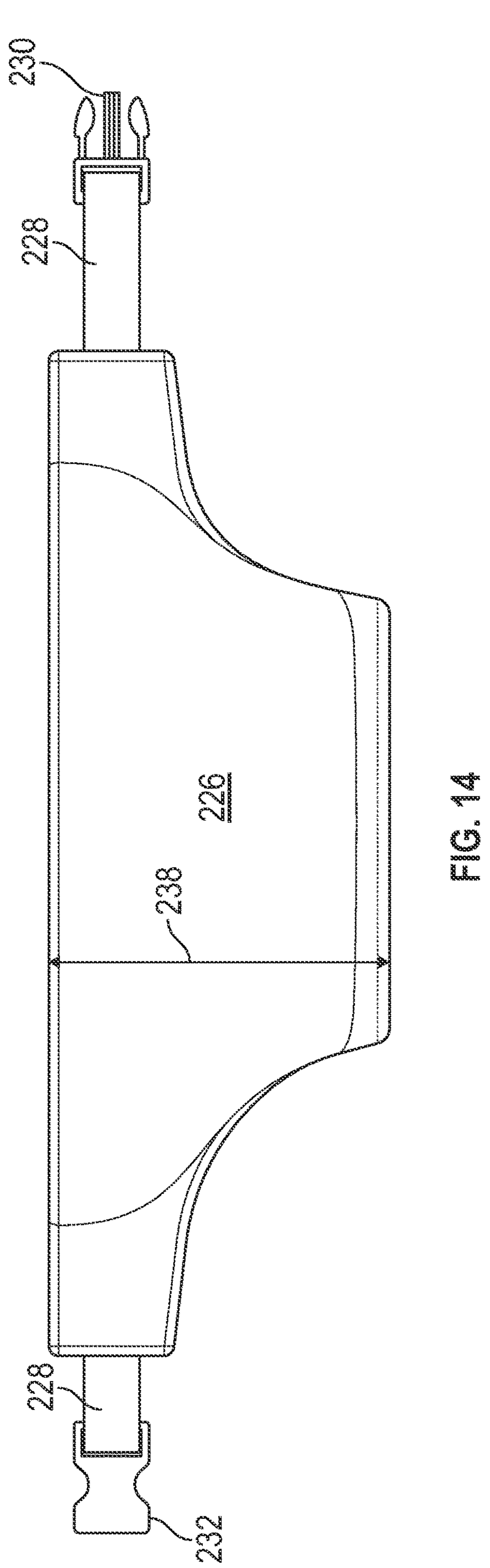
FIG. 14 is a rear view of the positioner of FIG. 11 in the open configuration.
Figure 15:
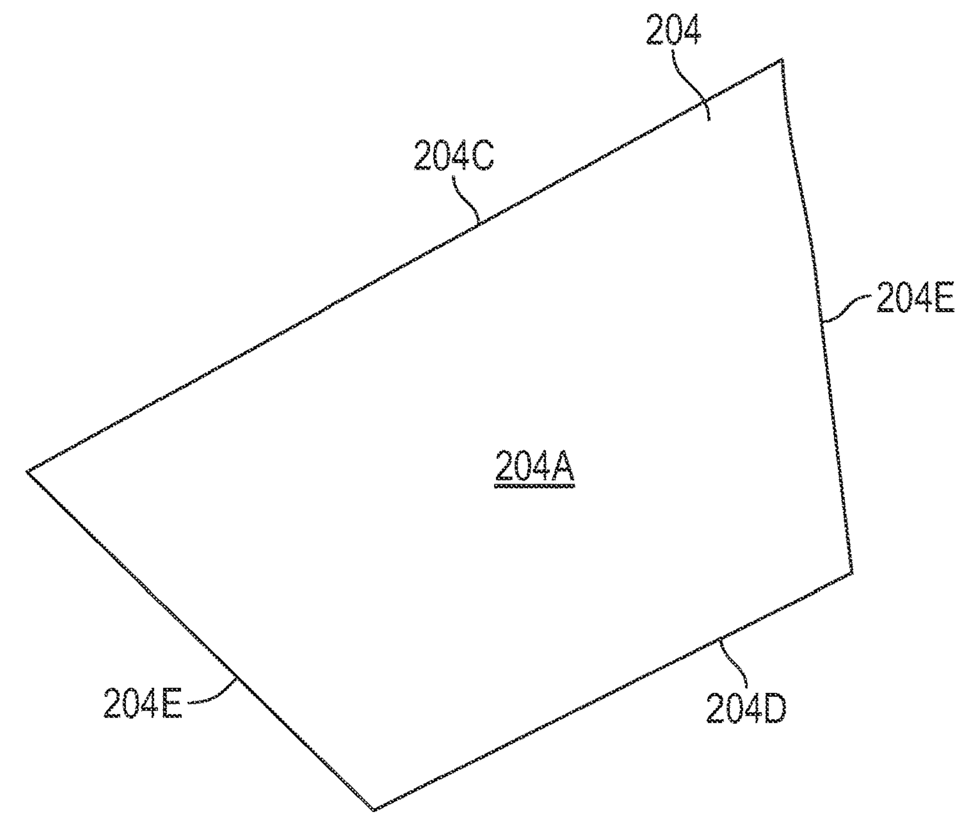
FIG. 15 is a front view of an implementation of a filler of the positioner of FIG. 11.
Figure 16:
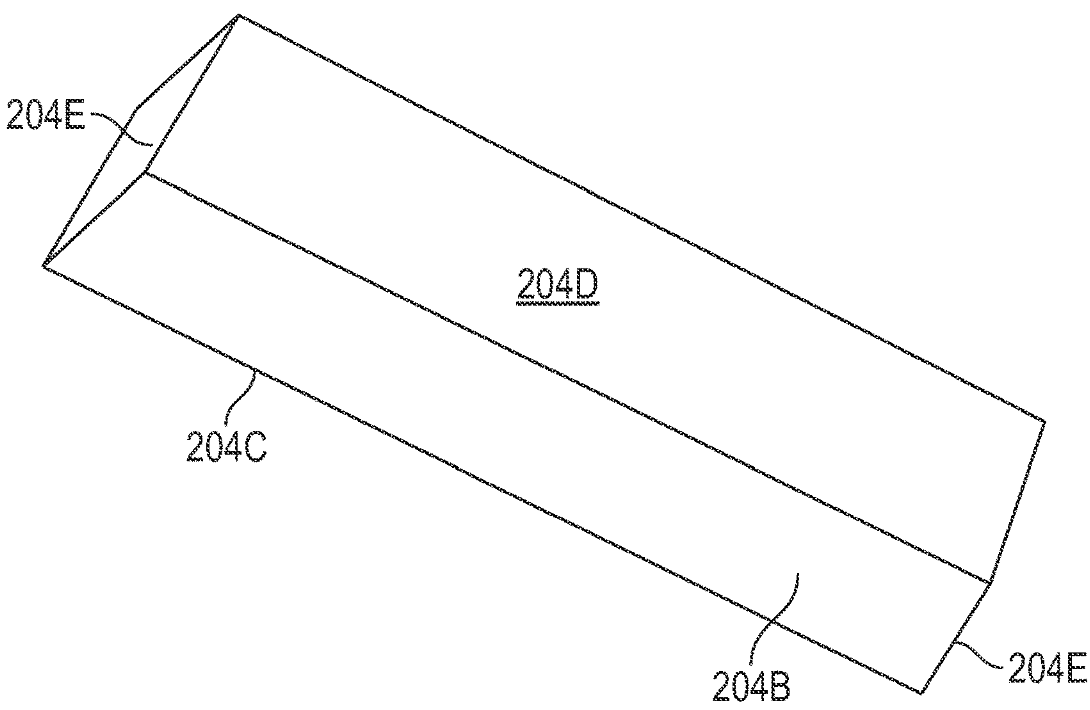
FIG. 16 is a bottom, rear, left-side view of the filler of FIG. 15.
Figure 17A:
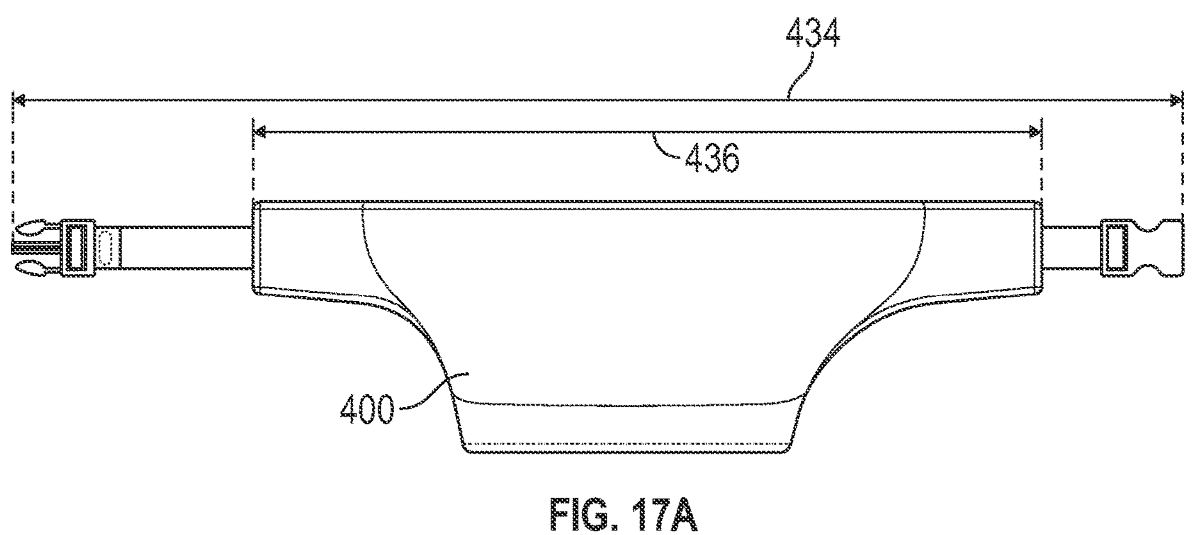
FIG. 17A is a front view of another implementation of a positioner in an open configuration, illustrating size comparisons relative to the positioners of FIGS. 17B and 17C.
Figure 17B:
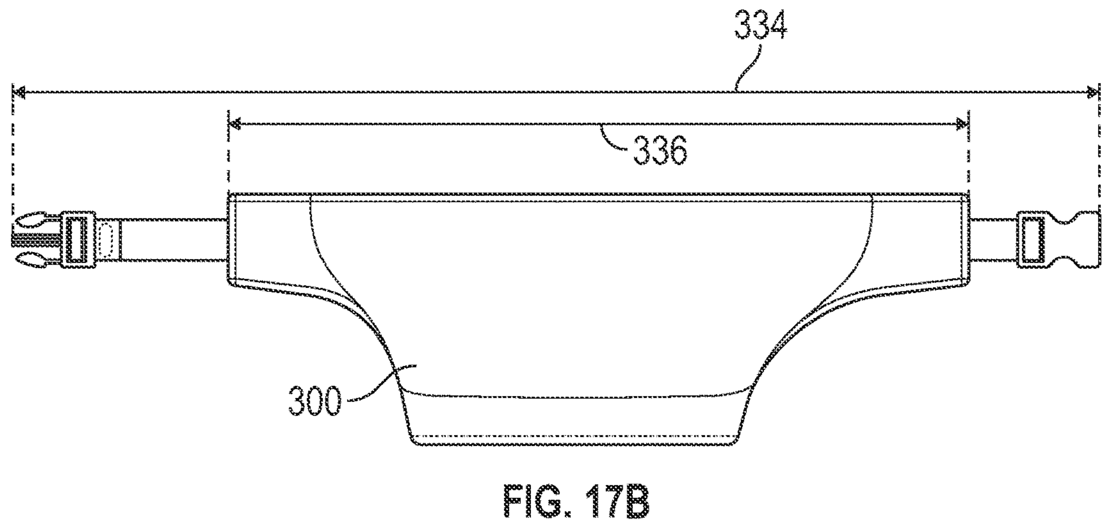
FIG. 17B is a front view of another implementation of a positioner in an open configuration, illustrating size comparisons relative to the positioners of FIGS. 17A and 17C.
Figure 17C:
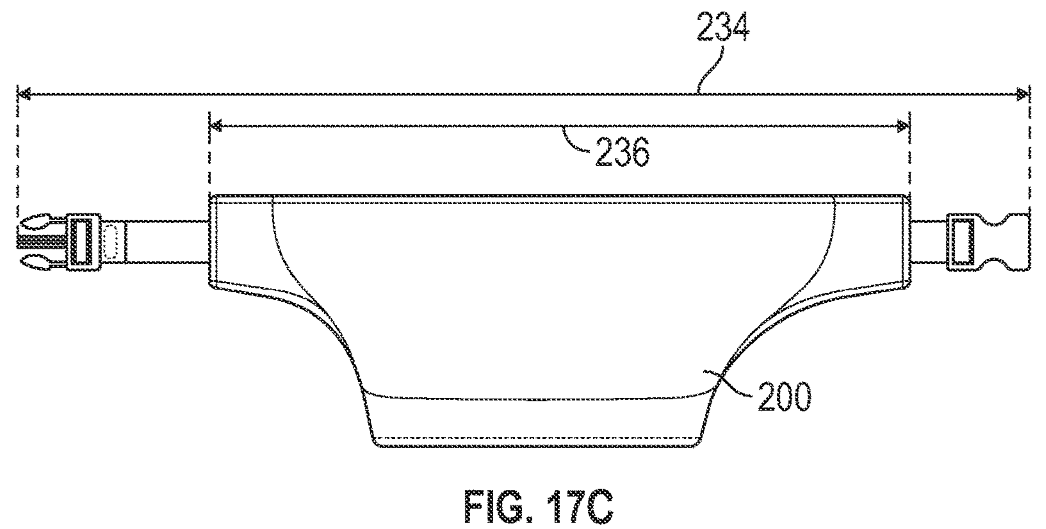
FIG. 17C is a front view of the positioner of FIG. 11 in the open configuration, illustrating size comparisons relative to the positioners of FIGS. 17A and 17B.

Referring now to FIGS. 11-17C, a second implementation of a positioner, and implementing components, are shown. FIG. 11 shows a top view of positioner 200 in an open configuration. FIG. 12 shows a front view of the positioner in the open configuration. FIG. 13 shows a bottom view of the positioner in the open configuration. FIG. 14 shows a rear view of the positioner in the open configuration. FIG. 15 shows a front view of a filler 204 of the positioner. FIG. 16 shows a bottom, rear, left-side view of the filler. FIG. 17C shows a front view of the positioner to show size comparisons relative to other positioners.

Positioner 200 includes a compressible member 202 having a covering 206, a main body 208, arms 210, curved sections 214, a straight or substantially straight section 216, a front 218, a top 220, a bottom 222, seams (including seam 224), and a back 226. Positioner 200 further includes straps 228 and couplers 230 and 232. Each of these elements is, in general, similar or identical to a similarly named element described above with respect to positioner 100, having similar or identical configurations and/or functions. However, the filler 204 has a different shape than filler 104—it is seen to not have arms (unlike filler 104) but to have a three-dimensional trapezoidal shape (i.e., the shape of a trapezoidal prism). The filler 204 is seen in FIGS. 15-16 to include a front 204A, back 204B, top 204C, bottom 204D, and sides 204E.

Filler 204 may be used with various coverings each of which has a similarly sized (or somewhat similarly sized) main body 208, but differently sized arms 210. In these implementations the filler fills the main body but does not fill (or only slightly or partially fills) the arms. This is useful for ease of manufacturing and assembly, in that it allows for differently sized positioners 200 (having various lengths 234/236) which may all use the same size of filler. In such implementations, the arms may not have the filler therein (or may only partially have the filler therein) but the arms may not need the filler therein to properly position a deceased person's head, neck, jaw, chin, and/or mouth-since the main body of the compressible member may be sufficient for such positioning. However, in some implementations, positioner 100, having the filler extending into the arms, may be more useful for more securely positioning a deceased person's head, neck, jaw, chin, and/or mouth, since having a filler fully within the arms may further keep the person's head from tilting to either side and/or may otherwise more securely support the head and other elements of the deceased person.

Filler 204 may be made of any of the materials described herein for filler 104, though in the examples in the drawings it is formed of a polymeric foam. Other shapes may be possible, and the three-dimensional trapezoidal shape (i.e., trapezoidal prism shape) is only one example.

Positioners 300 and 400 are shown in FIGS. 17B and 17C, respectively, and while these have different overall lengths and compressible member lengths relative to positioner 200, each of positioners 200/300/400 includes the same filler 204. Accordingly, filler 204 is useful for ease of manufacturing and assembly, wherein various sizes/shapes of positioners may include the same filler. With positioner 100 the filler 104 may actually be sized and shaped to fully extend into each arm, so that the full covering is filled with the filler. With positioners 200, 300 and 400 the filler may fill only the main body and a portion of each arm, or none of each arm.

In implementations the fillers may be sized and shaped so that they are slightly more voluminous, in a non-compressed state, than the internal volume of the covering-such that the filler is in a state of compression when secured within the covering due to the covering pressing against it. This compression may increase the firmness of the compressible member. In other implementations the filler in a non-compressed state could be less voluminous than (or only as voluminous as) the internal volume of the compressible member, which may result in a less firm compressible member. These characteristics may be adjusted as desired, to achieve desired compressible member firmness. The materials of the filler may also be changed, varied, or adjusted to adjust firmness or other characteristics.

FIGS. 17A-17C, as indicated, show positioners 200, 300 and 400 which have different overall lengths and compressible member lengths but which use the same filler (FIGS. 11 and 14 also illustrate a height and thickness of positioner 200).

Example dimensions of positioner 200 are: an overall length 234 (straps fully extended) of 21 inches; a compressible member length 236 of 14 inches; a height 238 of 5 inches; a thickness 240 of 1⅜ inches; and a circumference of the compressible member measured around its bottom and top of 11¼ inches.

Example dimensions of positioner 300 are: an overall length 334 (straps fully extended) of 22 inches; a length 336 of 15½ inches; a height (measured in the same direction as height 238) of 5 inches; a thickness (measured in the same direction as thickness 240) of 1⅜ inches; and a circumference of the compressible member measured around its bottom and top of 11¼ inches.

Example dimensions of positioner 400 are: an overall length 434 (straps fully extended) of 25 inches; a length 436 of 18 inches; a height (measured in the same direction as height 238) of 5⅜ inches; a thickness (measured in the same direction as thickness 240) of 1¼ inches; and a circumference of the compressible member measured around its bottom and top of 11½ inches.

Example dimensions for positioner 100 may be the same or similar to those of positioner 400 (positioner 100 may be a large size), including: an overall length 134 (straps fully extended) the same as length 434; a length 136 the same as length 436; a height 138 of 5⅜ inches; and a thickness 140 of 1¼ inches.

There may be medium and small versions of positioner 100, with smaller dimensions (including dimensions equal or similar to positioner 300 and 200, respectively). To accommodate this, the filler 104 may be modified. For example, the dimensions of the large filler 104 may be sized to have a 1¾ inch thickness between the front 104A and back 104B, a circumference of each arm (about 3 inches from the side 104F) of about 8 inches, a 13½ inch circumference measured around the top 104D and bottom 104E, and a length between sides 104F of 17¾ inches. This filler may be modified by removing 1 inch from each arm (1 inch in from each side 104F) for a medium version, or by removing 2 inches from each arm (2 inches in from each side 104F) for a small version. In implementations coverings used for small, medium, and large positioners, with the filler 104 or modified versions thereof, may be the same coverings used for the small, medium, and large positioners 200, 300, and 400, respectively.

It is believed that the medium size positioners may be the default or most-used sizes based on common deceased-person body sizes. In implementations wherein the fillers are formed of foam they may be stamped out of a foam sheet or the like, though other fabrication techniques may be used.

In experimentation it was found that the small and medium positioners 200 and 300 worked well notwithstanding not having filler in (or not having filler fully in) the arms, though experiments with the large positioner 400 seemed to indicate that a large positioner 100 with the arms having filler therein may work better.

For positioner 200 each arm has a circumference, measured about 3 inches in from the terminal end of the arm, of about 4⅜ to 6⅜ inches. For positioner 200 there is a 1⅝ inch gap from the side 204E of the filler to the corresponding terminal end of the arm.

For positioner 300 each arm has a circumference, measured about 3 inches in from the terminal end of the arm, of about 5 to 7 inches. For positioner 300 there is a 3½ inch gap from the side 204E of the filler to the corresponding terminal end of the arm.

For positioner 400 each arm has a circumference, measured about 3 inches in from the terminal end of the arm, of about 6 to 8 inches. For positioner 400 there is a 4 inch gap from the side 204E of the filler to the corresponding terminal end of the arm.

In implementations the straps 128/228 are formed of elastic material so that they allow some stretching. In other implementations they may be formed of non-elastic materials. "Elastic material" is defined herein as any material which elastically deforms more than 20% along any dimension. An elastic material may comprise a single material type or may be a composite of multiple elements—for example an elastic material rubber core surrounded with a cloth or fabric elastic material or non-elastic material sleeve.

In some cases, instead of having a T-shape as shown in the drawings, the compressible member could have a shape of a cylinder with varying diameter. For example the cylinder could have a maximum diameter at its center, positioned below the chin of the deceased person, and could have a narrower diameter at the arms. Even so, the T-shape may be useful in that it is not likely to roll and slip during use due to its T-shape.

In experiments it has been found that each arm of the T-shape is shaped and sized to rest within a divot formed between the person's neck and collar bone. This helps to keep the positioner stable and secure when in use, so that it does not slip or move but stays in a desired position. This also helps to keep the main body abutting the neck, the bottom of the jaw, and the very top of the person's chest.

Although the implementations in the drawings show the couplers clasped or buckled at the back of the deceased person's neck, some implementations may be configured to be clasped or buckled at the side of the person's neck. This has the advantage of easier placement of the positioner on a deceased person, since the deceased person's head may not need to be raised at all, or at least may not need to be raised while buckling the couplers. However, such a configuration may necessitate not having an arm at one side, or may necessitate changes to the arm, which may make it more likely for the positioner to slip or move during use. Accordingly, while the positioner versions in the drawings may require raising the deceased person's head during buckling and/or tightening of the positioner, it may also result in a more stable configuration wherein the positioner does not move thereafter.

Some seams may be excluded in some versions. For example, the bottom seam 124 (and corresponding seams in other versions) may be excluded and, instead, there may be an opening at the bottom of the covering which has a flap with one or more button closures. This may allow the user to fill the covering with the filler and, thereafter, to close the opening by folding the flap over the opening and securing the one or more buttons. In some implementations this type of configuration may result in simpler and/or less expensive manufacturing. Instead of buttons, the covering may use a zipper, snaps, magnets, a resealable adhesive, hook-and-loop fasteners, or any other closure mechanisms to releasably close any opening.

The various devices and/or assemblies disclosed herein and their elements, sub-elements, sub-assemblies, and so forth may be formed from any materials that will feasibly allow, facilitate, and/or otherwise not hinder their respective functions as described herein. For example, any of the devices, elements, or sub-elements may, wherever possible, be formed of metals, polymers, composites, ceramic materials, fabrics, and so forth.

Furthermore, there are a variety of ways in which the various elements may be directly or indirectly coupled together. Notwithstanding the specific ways in which elements are depicted as being coupled together herein, these same elements could, wherever feasible, be joined together in any of the following ways: manually removably coupled together such as using a friction fit, hook and loop fasteners, snaps, buttons and corresponding holes, zippers, a reusable adhesive, and any other type of manually removable coupling mechanism; or fixedly/permanently coupled together such as using a permanent adhesive, rivets, melt joining or heat bonding, sewn elements, stitching, seams, and any other type of permanent coupling mechanism that is not manually removable. Manually removable, as defined herein, refers to the ability to remove a coupling using manual force either using hands alone or using non-powered hand tools (i.e., tools powered only by the user's hands).

The above-described elements may in implementations be configured or arranged in a variety of arrangements, each arrangement with its own advantages as will be understood by the practitioner of ordinary skill in the art, notwithstanding the specific example arrangements which are discussed above and representatively illustrated in the drawings.

Furthermore, while each individual above-described element may be configured as shown in the drawings and/or as discussed above, these are only representative examples and other configurations are possible for any individual element, with various advantages and tradeoffs as will be understood by the practitioner of ordinary skill in the art.

In places where the phrase "one of A and B" is used herein, including in the claims, wherein A and B are elements, the phrase shall have the meaning "A and/or B." This shall be extrapolated to as many elements as are recited in this manner, for example the phrase "one of A, B, and C" shall mean "A, B, and/or C," and so forth. To further clarify, the phrase "one of A, B, and C" would include implementations having: A only; B only; C only; A and B but not C; A and C but not B; B and C but not A; and A and B and C.

In places where the description above refers to specific implementations of positioners and related methods, one or more or many modifications may be made without departing from the spirit and scope thereof. Details of any specific implementation/embodiment described herein may, wherever possible, be applied to any other specific implementation/embodiment described herein. The appended claims are to encompass within their scope all such changes and modifications as are within the true spirit and scope of this disclosure.

Furthermore, in the claims, if a specific number of an element is intended, such will be explicitly recited, and in the absence of such explicit recitation no such limitation exists. For example, the claims may include phrases such as "at least one" and "one or more" to introduce claim elements. The use of such phrases should not be construed to imply that the introduction of any other claim element by the indefinite article "a" or "an" limits that claim to only one such element, and the same holds true for the use in the claims of definite articles.

Additionally, in places where a claim below uses the term "first" as applied to an element, this does not imply that the claim requires a second (or more) of that element-if the claim does not explicitly recite a "second" of that element, the claim does not require a "second" of that element. Furthermore, in some cases a claim may recite a "second" or "third" or "fourth" (or so on) of an element, and this does not necessarily imply that the claim requires a first (or so on) of that element-if the claim does not explicitly recite a "first" (or so on) of that element (or an element with the same name, such as "a widget" and "a second widget"), then the claim does not require a "first" (or so on) of that element.

Method steps disclosed anywhere herein, including in the claims, may be performed in any feasible/possible order. Recitation of method steps in any given order in the claims or elsewhere does not imply that the steps must be performed in that order-such claims and descriptions are intended to cover the steps performed in any order except any orders which are technically impossible or not feasible. However, in some implementations method steps may be performed in the order(s) in which the steps are presented herein, including any order(s) presented in the claims.

As used herein, the term "compressible" may in implementations have the meaning of being able to be compressed at least 10% in at least one direction using manual force alone. In other implementations "compressible" may have the meaning of being able to be compressed at least 20% in at least one direction using manual force alone. The phrase "manual force" in implementations refers to a force at or below 20 pounds of force. The phrase "manual force" in implementations refers to a force at or below 40 pounds of force.

The terms "substantial" and "substantially," as used herein, in implementations have the meaning of at least 80% of the degree, volume, measurement, etc. referenced. For example, a filler "substantially" fills the main body of the compressible member if it fills 80% or more of the total possible volume of the main body (this is the case even if the filler itself has low density—thus a foam comprising some air nevertheless substantially fills the main body if it expands and/or holds the main body to a volume of at least 80% of a total possible volume of the main body when in a resting configuration and not under pressure/force). Similarly, the filler substantially fills the arms if it expands each arm to 80% of its total possible volume. In implementations the filler does not extend into the arms, or fills less than 20% of each arm (meaning it expands the volume of each arm to no more than 20% of its total possible volume), or fills less than 30% of each arm, or less than 40% of each arm, or less than 50% (less than half) of each arm, or less than 60% of each arm, or less than 70% of each arm, or less than 80% of each arm, or less than 90% of each arm. The phrase "total possible volume" used in this paragraph refers to the concept that when an arm or main body has no filler therein (or is only partially filled therein) it could have a lower volume whereas when the filler completely fills the main body or the arms it forces the main body and/or arms to their maximum or "total" possible volumes.

As used herein the term "fabric" is defined as a material having a smallest thickness no greater than 3 mm, and being formed of polymeric film and/or woven fibers and/or otherwise joined/coupled fibers, and capable of being formed into the covering shapes shown in the drawings.

Referring to FIGS. 2 and 4, in implementations the main body is defined vertically from top 120 to bottom 122 and is defined horizontally between boundaries 144 (each boundary 144 being simply a vertical imaginary line perpendicular with the top 120 and also contacting a location where the bottom 122 meets the curved section 114). In other words, in implementations the main body does not comprise the curved sections 114. In implementations each arm is defined vertically from top 120 to the below curved section 114 and is defined horizontally as the full length having the proximate curved section 114 below it- or in other words the full horizontal length from the boundary 144 to the terminal end 146 of the respective arm. Using these definitions, the average height (of all heights parallel with height 138) from top to bottom of the main body (and perpendicular with the top) is greater than the average height of each arm from top to bottom of the arm (and perpendicular with the top). The main body correspondingly has a greater average circumference from top to bottom (and perpendicular with the top) than an average circumference of either arm from top to bottom of the arm (and perpendicular with the top). Naturally, the curved section 114 of each arm is herein called the bottom of the arm, and the bottom of each arm in implementations may not form a curved section, but in some cases the curved section is useful for allowing the arms to properly fit around the neck and between the head and collar bone of the deceased person.

Example circumference 148 represents a single circumference of one of the arms taken at a single location, the circumference circumscribing the top 120 and bottom (i.e., curved section) of the arm, and being parallel with the top 120. As will be understood by the practitioner of ordinary skill in the art, the average circumference of either arm could be found by averaging the circumferences along the respective arm between the respective boundary 144 and terminal end 146 that are parallel with example circumference 148. Although example circumference 148 is not shown other than in FIG. 4, as circumferences are easy to understand the practitioner of ordinary skill in the art will understand where example circumference (and other parallel circumferences taken along the same arm) would be taken/measured with respect to other drawings. Example circumference 142 of the main body similarly represents a single circumference taken from top to bottom, and parallel with the top, and the practitioner of ordinary skill in the art will understand how to determine the average circumference of all circumferences of the main body parallel with circumference 142 between the boundaries 144. It is also pointed out that, even visually without doing any measurement, the practitioner of ordinary skill could relatively easily perceive from the drawings that the main body of each example positioner has an average circumference from top to bottom (taken perpendicular with the top) that is greater than an average circumference from top to bottom (taken perpendicular with the top) of either arm.

The above example definitions for the main body and arms are only representative examples, and in other implementations the main body and arms could be defined in other ways. Similarly, some implementations could have different configurations with respect to average heights and circumferences, though the examples given herein have the advantages described herein.

It is further pointed out that, although the deceased person's collar bone (and divot between the neck and collar bone) are not explicitly pointed out in the drawings, it is well understood in the art how to locate a deceased person's collar bone, neck, associated divot therebetween, and so forth, so that the description and drawings are sufficient for enablement of the invention and so that the practitioner of ordinary skill in the art would understand the metes and bounds of each claim.

In implementations wherein the couplers or buckles are secured together at the back of the deceased person's neck they may not be visible during a funeral viewing because they may be obscured by the deceased person's head/neck/clothing and/or pillows or pillow-like elements within a casket or forming part of the casket. This improves aesthetics during the funeral viewing by keeping the buckles/couplers hidden.

When the positioner is secured around a deceased person's neck as shown in the drawings it secures the deceased person's mouth closed and further keeps the head of the deceased person in a substantially fixed position, both of which are desirable for a funeral viewing.

The example fillers shown in the drawings are each formed of a single solid piece of compressible material (foam, in each case), though in other implementations the fillers could be formed of other materials (and need not be formed entirely of a single piece of material), as described herein, though there are advantages and tradeoffs to each configuration. Using a single piece of material, for example, allows for ease of manufacture/assembly and, as described herein, may allow for using the same size of filler for multiple sizes of coverings without difficulty.

In implementations the positioners disclosed herein may be used to reduce or eliminate snoring, during sleep, of a living person. This may in part be accomplished by keeping the sleeping person's mouth closed and/or head positioned in a desired position. Keeping the mouth closed may additionally help to keep the person's tongue seated against the front teeth of the sleeper or otherwise positioned in such a way that snoring is reduced or eliminated. The positioners disclosed herein could be used with or without associated continuous positive airway pressure (CPAP) equipment.

What is claimed is:

1. A positioner, comprising:

a compressible member forming a main body and two arms each extending from the main body, the compressible member also forming a top;

wherein the main body has an average circumference circumscribing the top and a bottom of the main body, and perpendicular with the top of the main body;

wherein each arm has an average circumference circumscribing the top and a bottom of the arm, and perpendicular with the top;

wherein the average circumference of the main body is greater than the average circumference of each arm; and wherein the compressible member comprises a covering at least partially filled with a filler; and a plurality of straps secured to the compressible member and extending therefrom;

wherein the positioner is configured to be secured around a neck of a person such that the main body secures a mouth of the person closed and the main body and arms position a head of the person in a substantially fixed position; and wherein the main body and the arms form a T-shape configured to keep the main body abutting the neck, a bottom of the person's jaw, and a top of the person's chest.

* * * * *